United States Patent [19]
Solomon et al.

[11] Patent Number: 5,645,539
[45] Date of Patent: Jul. 8, 1997

[54] ELONGATED MEDICAL CHANNEL ASSEMBLY AND METHOD OF PREVENTING DISLODGEMENT

[75] Inventors: Lewis S. Solomon, Santa Rosa; Peter D. Dieterich, Jr., Corte Madera, both of Calif.

[73] Assignee: Innocare One, Ltd., Sausalito, Calif.

[21] Appl. No.: 338,647

[22] Filed: Nov. 14, 1994

[51] Int. Cl.$^6$ ................................ A61M 25/00
[52] U.S. Cl. .................. 604/283; 604/174; 604/280; 604/905
[58] Field of Search ................ 604/22, 35, 43, 604/54, 77, 86, 93–95, 119–121, 126, 128, 159, 174–178, 180, 183, 194, 244, 264, 270, 280, 283, 307, 905; 606/198, 201; 128/642, 207.18, DIG. 15, DIG. 26, 202.27; 607/57; 285/261, 921; 137/614.05; 251/148

[56] References Cited

U.S. PATENT DOCUMENTS

| | | |
|---|---|---|
| Re. 25,788 | 6/1965 | Sheridan . |
| 103,567 | 5/1870 | Coar ...................... 285/261 |
| 1,748,817 | 2/1930 | Zerk ................... 137/614.05 |
| 2,874,981 | 2/1959 | Brady . |
| 3,021,842 | 2/1962 | Flood ........................ 128/215 |
| 3,401,690 | 9/1968 | Martin ..................... 128/172.1 |
| 3,707,972 | 1/1973 | Villari et al. . |
| 3,823,720 | 7/1974 | Tribble ................... 128/350 R |
| 3,951,153 | 4/1976 | Leucci ................... 128/349 R |
| 4,294,247 | 10/1981 | Carter et al. . |
| 4,338,933 | 7/1982 | Bayard et al. . |
| 4,375,811 | 3/1983 | Sabbota et al. ............... 604/97 |
| 4,511,163 | 4/1985 | Harris et al. . |
| 4,516,970 | 5/1985 | Kaufman et al. . |
| 4,613,323 | 9/1986 | Norton et al. .............. 604/43 |
| 4,631,054 | 12/1986 | Kim .......................... 604/54 |
| 4,636,204 | 1/1987 | Christopherson et al. . |
| 4,645,492 | 2/1987 | Weeks ...................... 604/174 |
| 4,660,555 | 4/1987 | Payton .................. 128/207.18 |

(List continued on next page.)

OTHER PUBLICATIONS

Meer, J.A., "Inadvertent Dislodgement of Nasoenteral Feeding Tubes: Incidence and Prevention", *Journal of Parenteral and Enteral Nutrition*, 11(2) :187–189 (1987).

Meer, J.A., "A New Nasal Bridle for Securing Nasoenteral Feeding Tubes", *Journal of Parenteral and Enteral Nutrition*, 13(3) :331–334 (1989).

McGuirt, W.F., et al., "'How I Do It'—Head and Neck; A Targeted Problem and Its Solution; Securing of Intermediate Duration Feeding Tubes", *The Laryngoscope*, 90:2046–2048 (1980).

Sax, H.C., et al., "A Method for Securing Nasogastric Tubes in Unco–Operative Patients", *Surgery, Gynecology & Obstetrics*, 164:471–472 (1987).

*Primary Examiner*—Michael Buiz
*Assistant Examiner*—Cris L. Rodriguez
*Attorney, Agent, or Firm*—Flehr Hohbach Test Albritton & Herbert LLP

[57] ABSTRACT

An elongated medical channel assembly (21, 121) including an indwelling channel-defining member (22, 122), an external channel-defining member (26, 126) and a coupling assembly (25, 125) coupling the channel-defining members together at a position along the length thereof substantially at an exit site (27, 127) of the channel assembly from a patient. The coupling assembly (25, 125) further is formed for uncoupling of the external member (26, 126) with a disconnect force less than the force required to dislodge the indwelling member (22, 122) from an indwelling position in the patient. The medical channel assembly can take the form of a tube assembly (21) having a coupling (25) formed to provide for multi-directional release, for example, as is provided by a ball (42) and socket (41) connection. Alternatively, a signal transmitting assembly (121) can be provided with a releasable coupling (125) can be provided with a releasable coupling (125) at the exit site (127). A method also is provided for preventing dislodgement, as well as a method for mounting the coupling assembly (25, 125) to an indwelling member (22, 122) so that the medical channel assembly length can be sized to the individual patient.

41 Claims, 6 Drawing Sheets

U.S. PATENT DOCUMENTS

| | | | |
|---|---|---|---|
| 4,778,448 | 10/1988 | Meer | 604/54 |
| 4,823,789 | 4/1989 | Beisang, III | 128/207.18 |
| 4,826,486 | 5/1989 | Palsrok et al. | |
| 4,834,706 | 5/1989 | Beck et al. | |
| 4,874,378 | 10/1989 | Hillstead | 604/167 |
| 4,932,943 | 6/1990 | Nowak | 604/180 |
| 4,950,254 | 8/1990 | Andersen et al. | |
| 5,047,021 | 9/1991 | Utterberg | |
| 5,078,170 | 1/1992 | Henry | 137/614.05 |
| 5,137,524 | 8/1992 | Lynn et al. | |
| 5,152,755 | 10/1992 | Yoshinori | |
| 5,156,603 | 10/1992 | Olsen | |
| 5,377,668 | 1/1995 | Ehmsen et al. | 128/4 |
| 5,402,826 | 4/1995 | Molnar et al. | 137/614.05 |
| 5,423,764 | 6/1995 | Fry | 604/187 |

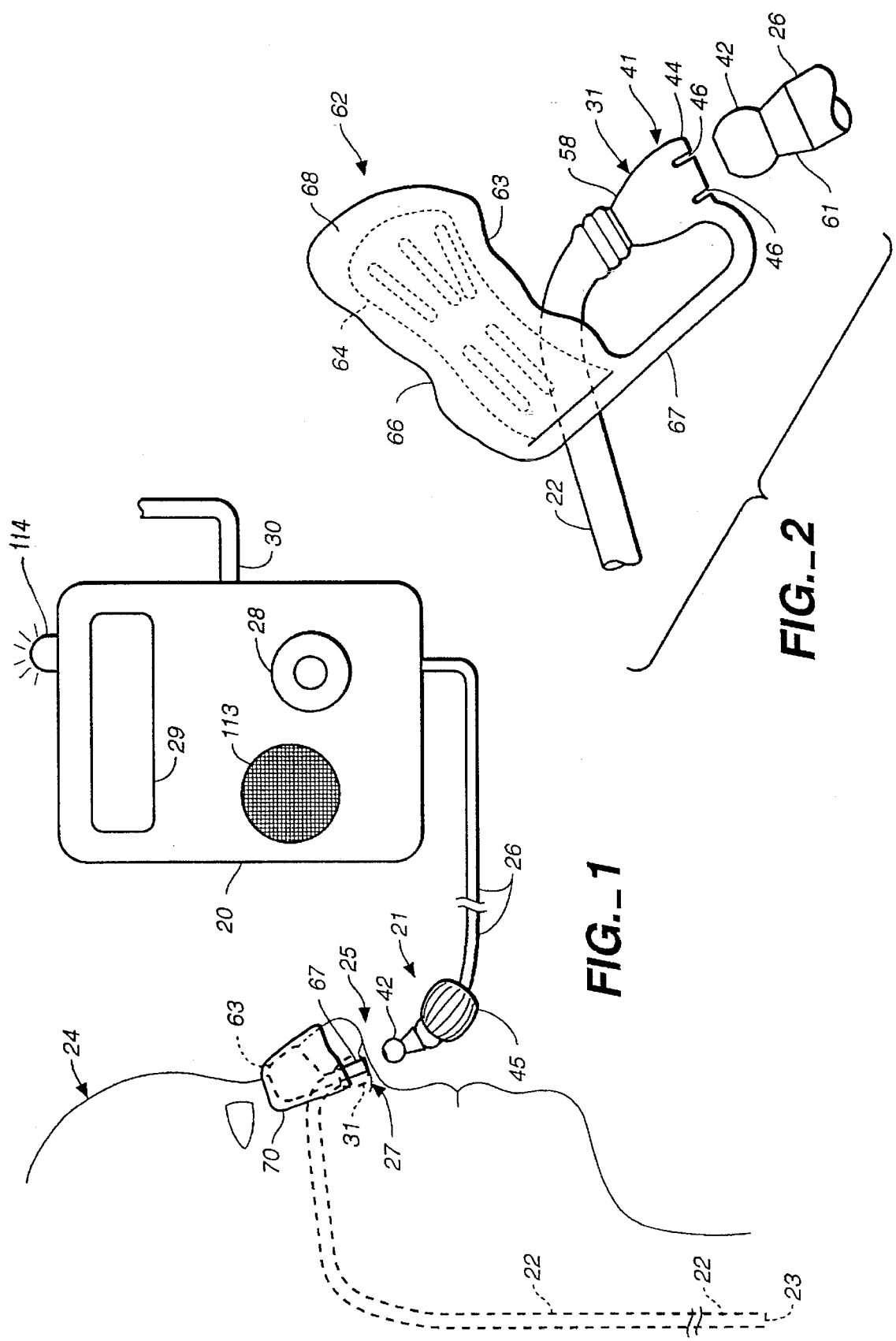

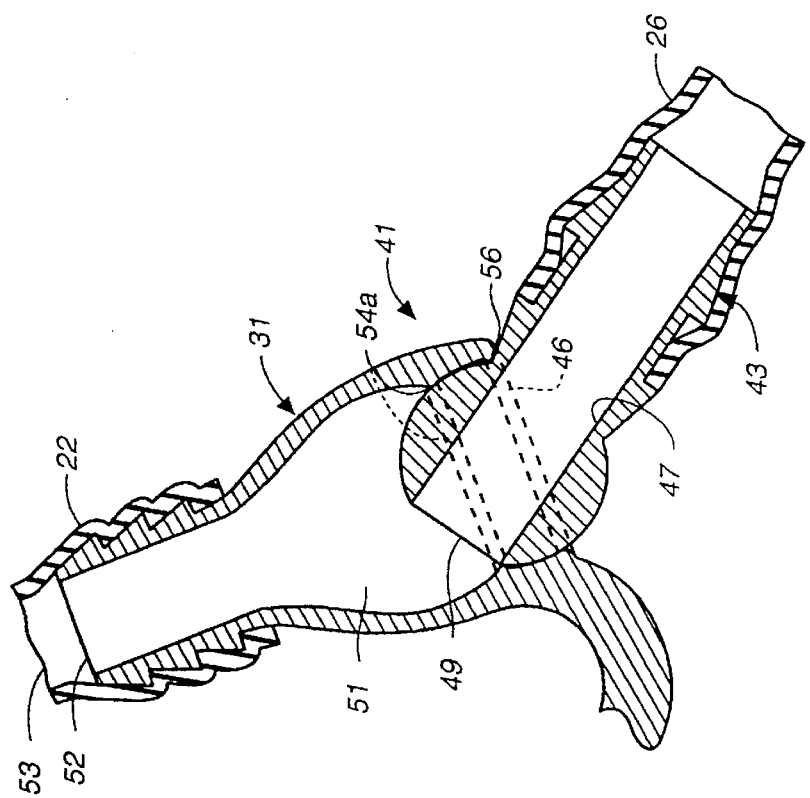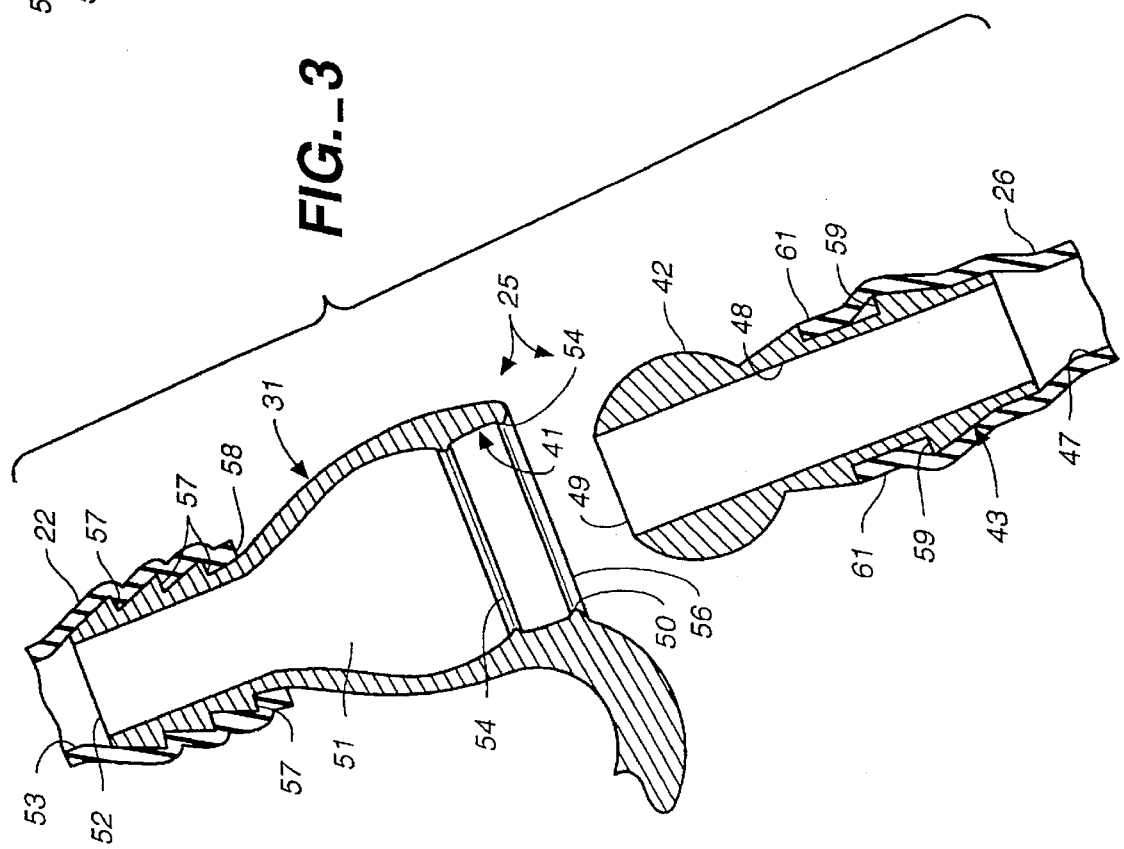

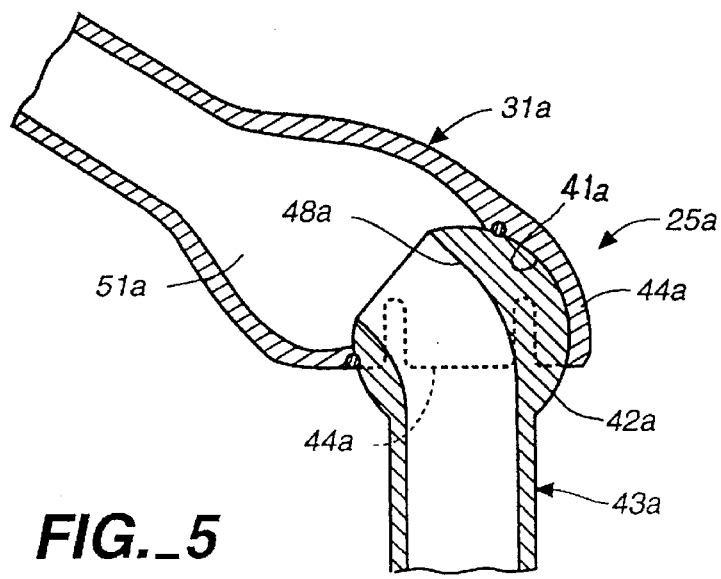
FIG._5
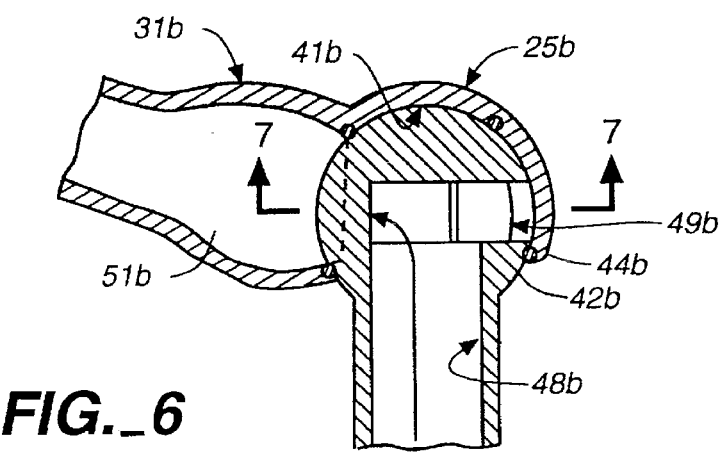
FIG._6
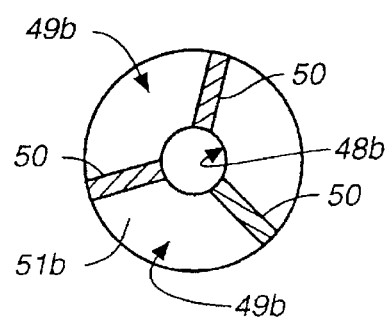
FIG._7

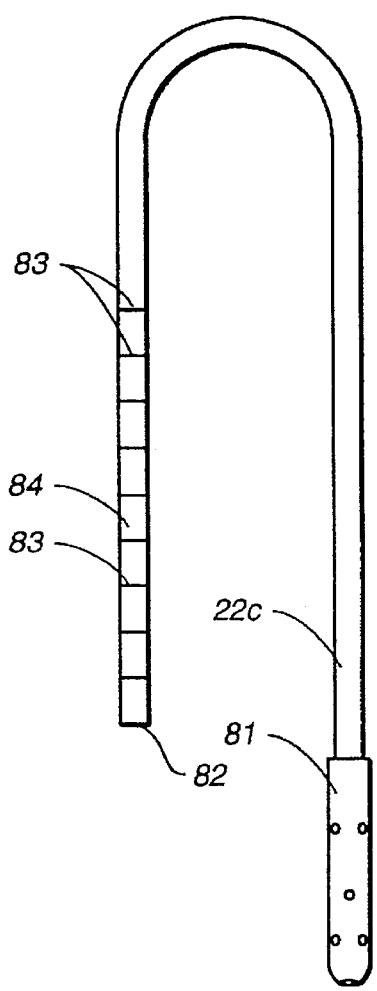
FIG._8
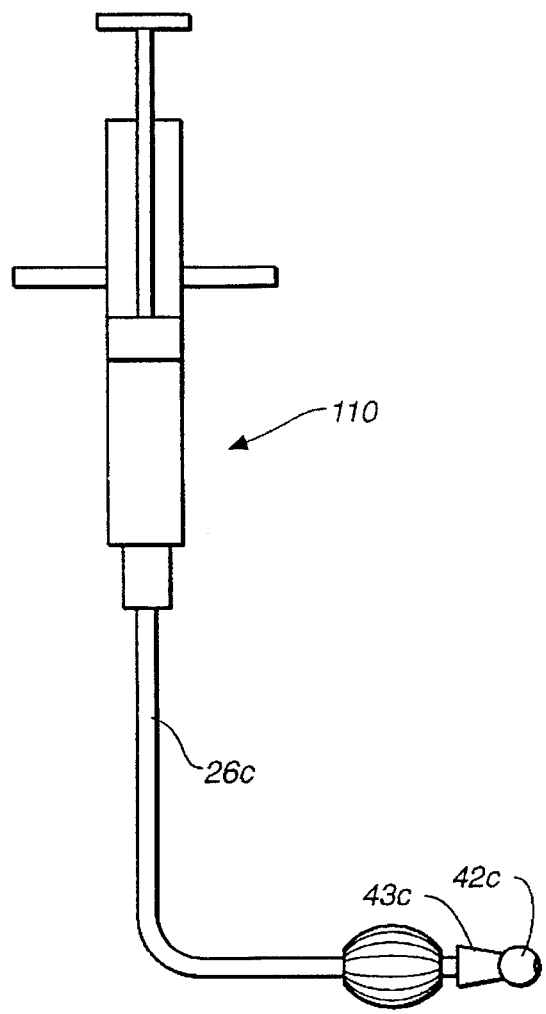
FIG._10
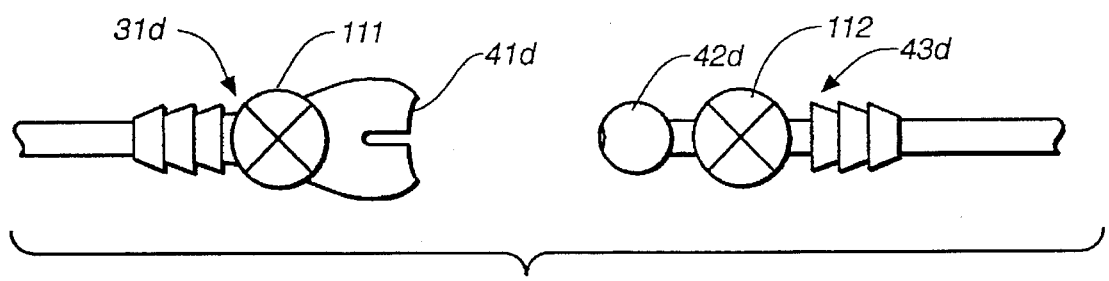
FIG._11

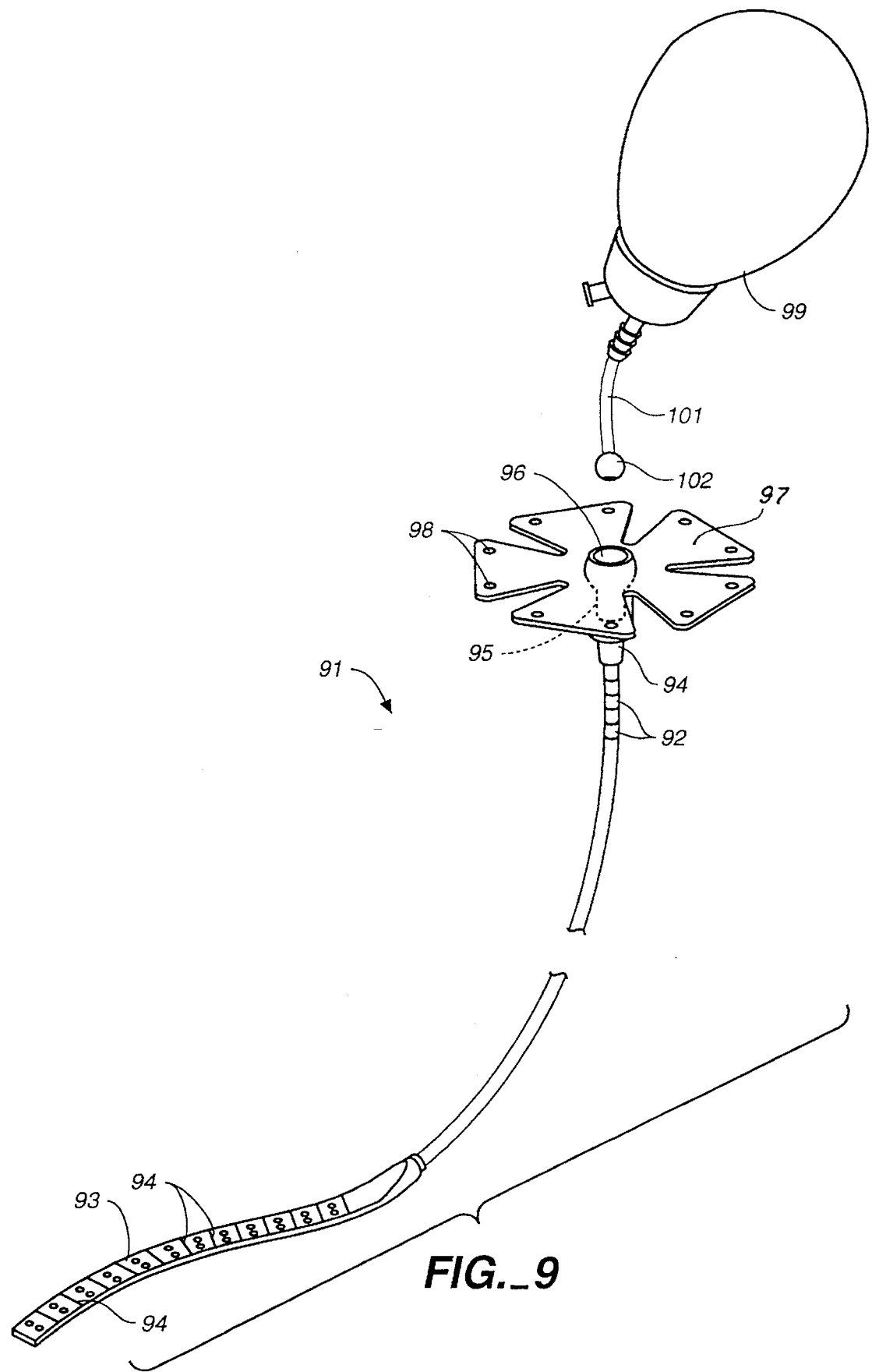
FIG._9

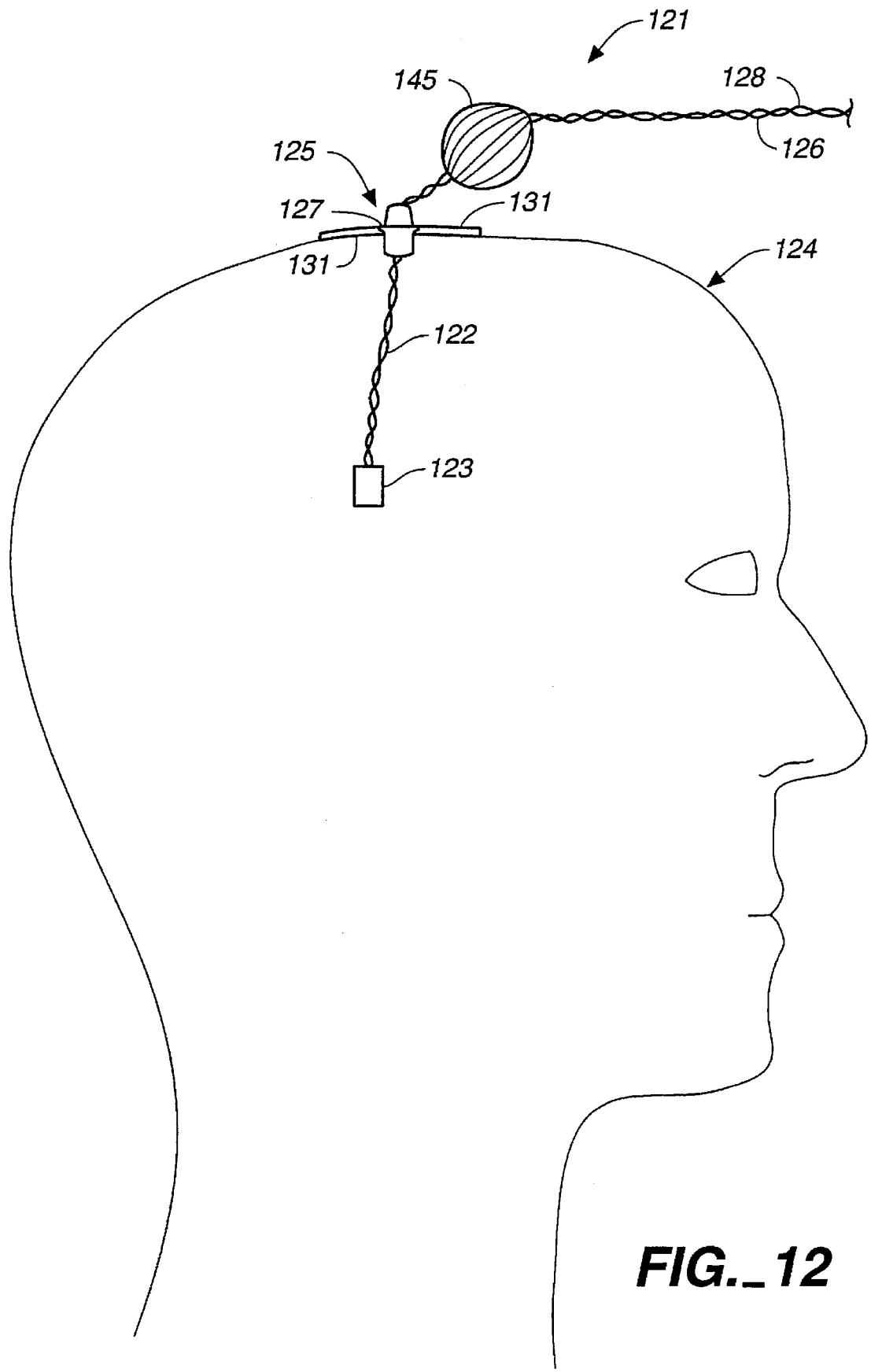
FIG._12

ELONGATED MEDICAL CHANNEL ASSEMBLY AND METHOD OF PREVENTING DISLODGEMENT

TECHNICAL FIELD

The present invention relates, in general, to elongated, medical channel assemblies, such as, catheters electrical monitoring lines and optical fiber assemblies, which are used for various medical procedures ranging from patient feeding to drainage, to monitoring, to stimulation. More particularly, the present invention relates to elongated channel assemblies for medical applications which are designed to prevent dislodgement, extirpation or removal of the channel assembly from the patient, either inadvertently or through deliberate patient intervention.

BACKGROUND ART

One of the most common medical applications for elongated, channel-assemblies is the use of a tube assembly for enteral feeding. Enteral feeding is the preferred method of providing nutritional support to the patient with a functional gastrointestinal tract. Enteral feeding has been proven to promote nitrogen retention, accelerate wound healing, and improve overall nutritional status. It is favored over intravenous feeding (total parenteral nutrition or TPN) because it helps to maintain intestinal integrity and has a lower infection risk. One of the major drawbacks to nasoenteral feeding, however, is the dislodgement of the tubes, the incidence of which has been documented to be 40 to 60%. The dislodgement of nasoenteral feeding tubes can have several negative repercussions:

(1) Nutritional support is interrupted, delaying wound healing and prolonging hospital stay.

(2) There is a substantial risk of aspiration pneumonia and respiratory failure when the tube is partially dislodged. In addition to the human suffering incurred with such a complication, expenses on the order of thousands of dollars per event per day are generated by antibiotic costs, intensive care and respiratory support. This complication is documented to occur in nearly one percent (0.8%) of the patients receiving a course of enteral nutrition.

(3) Replacement of dislodged nasoenteral feeding tubes is uncomfortable for patients and generates additional expenses due to physician and nursing time consumed, materials costs and procedural costs (including radiographic confirmation of tube placement).

(4) Caregivers may resort to intravenous nutrition which has a much higher risk of infection but is easier to secure.

(5) The above complications increase the risk of medical malpractice litigation.

The current trend in medicine towards managed care will also put pressure on hospitals to reduce complication rates, which will be tracked. Hospitals with excess complications will be excluded from contracts with large health care purchasers. Leaner staffing is also certain to be a byproduct of managed care. This means there will be less supervision of patients with feeding tubes. Not only will dislodgements increase in this setting, but they will be discovered later, making aspiration more likely. Replacing dislodged tubes will strain a lean staff even further.

Nasoenteral feeding maintains the dominant position in the nutritional support market due to its lower cost and incidence of infection relative to intravenous nutrition. Although most people can adapt to the presence of a small bore feeding tube once inserted, the actual placement is universally despised by patients. Nasogastric or nasojejunal intubation is often accompanied by retching, tearing, apprehension and verbal protests. Confused or combative patients strenuously resist tube placement requiring additional staff or restraint. This group of patients dislodge their feeding tubes with such regularity that the more easily secured parenteral route is often selected. By achieving a substantial reduction in the rate of inadvertent and uncooperative dislodgement, many of these patients could be successfully fed enterally.

Efforts to address this problem to date have focused on anchoring of the nasoenteral feeding tubes to resist patient removal. See, e.g., Sax, et al., "A Method For Securing Nasogastric Tubes In Unco-Operative Patients", Surgery, Gynecology & Obstetrics, May, 1987, pp. 471 and 472; McGuirt, et al., "Securing Of Intermediate Duration Feeding Tubes," The Laryngoscope, Vol. 90, 1980, pp. 2046–2048; Meer, "A New Nasal Bridle For Securing Nasoenteral Feeding Tubes", Journal Of Parenteral And Enteral Nutrition, Vol. 13, No. 3, 1989, pp. 331–334; and Meer, "Inadvertent Dislodgement Of Nasoenteral Feeding Tubes: Incidence And Prevention," Journal of Parenteral and Enteral Nutrition, Vol. 11, No. 2, 1987, pp. 187–189. The standard procedure involves taping the tube to the nose, but, as above noted, this procedure still is accompanied by the 40 to 60% removal or dislodgement rates. The additional use of wrist restraints or bulky mittens to deter inadvertent and uncooperative patient removal of the tubes has been frustrated by the "uncanny" ability of even confused patients to dislodge the tubes. The more drastic measures attempting to secure the tubes have included actual suturing of the tube through the nasal columella which can cause local infections and damage to the columella. Another approach is to use a "nasal bridle." Infrequent use of the nasal bridles is likely due to the numerous associated disadvantages. Placement of a nasal bridle requires from 10 to as much as 35 minutes of a skilled physician's time and can be quite difficult in uncooperative patients. Patient discomfort and the prospect of a patient injuring the nasal septum through vigorous tugging on the tube are also substantial drawbacks.

Removal, dislodgement or extirpation of medical channel-defining assemblies is not limited to enteral feeding tubes. Virtually any medical tube assembly which is mounted to a patient for an extended period of time for the administration of medicine, food or oxygen; the performance of medical procedures; or the drainage of fluids, can be dislodged either inadvertently by the caregiver during patient transport etc., or by confused, obtunded or otherwise uncooperative patients. Post-operative dislodgement of such tubes can be particularly serious, causing morbidity or even mortality.

One example of a traumatic medical tube assembly dislodgement problem occurs in connection with Foley-type urinary catheters. The Foley catheter is anchored in place by a balloon which is inflated once the end of the catheter is inside the bladder. Nevertheless, inadvertent and/or uncooperative patient dislodgements or extirpations occur in which the catheter is forcefully withdrawn through the urethra by the patient while the balloon is still inflated. This can cause the patient substantial discomfort and dangerous trauma with long-term effects.

Attempts recently have been made to prevent Foley catheter extirpation. A releasable connection has been suggested for use between the Foley catheter and the external drainage tube to the urine collection reservoir. This Foley disconnect assembly while representing a step forward, has several disadvantages. First, it is located at a substantial distance from the catheter's entry into the patient. Thus, even after disconnection, the uncooperative, obtunded or sedated patient still has an easily grasped catheter end, with a portion of the coupling thereon, which can be used to extirpate the catheter. Second, the Foley disconnect assembly is not designed to be secured externally to the patient and the coupling structure is essentially unidirectional, that is, the connection must be axially pulled to separate. Thus, if secured externally to the patient, for example by tape, the unidirectional coupling may fail to disconnect if the tubing is pulled in the wrong direction, resulting in possible pulling off of the securement device, dislodgement of the tubing and exposure of the patient to substantial stresses. If not secured, the coupling provides an easily gripped end on the tube assembly which the patient can use to extirpate the catheter. Moreover, the release force in the Foley disconnect assembly is sufficiently high that the connection would not be well suited for use in applications in which there was no balloon anchor on the catheter, for example, for enteral feeding tube applications.

Various other medical tube assemblies are known in the prior art in which connections or couplings have been interposed between an indwelling catheter and an external administering or drainage tube. Typical of medical tube assemblies having latched or locked couplings that can be manually released by a physician or technician are the devices of U.S. Pat. Nos. 5,137,524, 4,826,486, 5,047,021 and 4,338,933. Such assemblies have also included shut-off valves, for example, as shown in U.S. Pat. Nos. 3,707,972, 4,950,254 and 5,156,603, and others have included frangible elements and/or disconnection structures, as shown in U.S. Pat. Nos. 5,152,755, 4,834,706 and 4,294,247. Still further, many catheter-external tube connections are primarily concerned with the problems of making the connection or making a sterile connection, such as U.S. Pat. Nos. Re. 27,788, 4,511,163, 2,874,981 and 4,636,204.

Still further the problem of dislodgement or extirpation of elongated medical channel assemblies is not limited to tubing assemblies. In monitoring and/or stimulation applications, channel-defining assemblies are similarly positioned in patients and present problems of inadvertent or uncooperative dislodgement. Thus, inter-cranial pressure monitoring is accomplished through implanted transducers which communicate to external monitoring devices through electrical lines so that electrical signals can pass from the transducer through the conductor or channel to the monitoring device. A similar optical monitoring can occur based upon the use of fiber optic strands.

Despite the best efforts to address the problem of the dislodgement of medical channel structures, the solutions to date have been ineffective for the most part or potentially injurious. Patients with altered mental status are consistently able to pull on the tubes, lines and fiber strands and dislodge them and/or traumatize themselves.

Moreover, complicated and impractical "solutions" annoy the medical staff, generate extra costs and place patients all risk.

Finally, when a medical channel assembly is dislodged, it is commonplace for the blame to be placed on the nurse responsible for that particular patient. Deserved or not, such a rebuke adds to the aura of stress surrounding the procedure. The unpleasantness of the procedure, for both patients and hospital staff, the lost time, the associated expense (particularly in connection with surgical drains) and the possibility that it will have to be repeated, makes the reinsertion of medical channel assemblies a strongly disliked medical procedure.

Accordingly, it is an object of the present invention to provide a medical channel assembly and method which significantly reduces patient dislodgement, extirpation or removal and thereby reduces patient trauma and associated expense and medical staff stress.

A further object of the present invention is to provide a medical channel assembly and method in which the patient grippable portions of the assembly are easily disconnected without removal of the indwelling portion of the assembly, leaving a difficult to grasp indwelling length of the assembly in the patient.

Another object of the present invention is to provide an elongated medical channel assembly and method in which release or disconnection of the external portion of the channel from the portion internal to the patient can be easily accomplished at a wide range of angles with minimal force transmission to the sensitive tissues at the entry site.

Another object of the present invention is to provide a medical channel assembly which can have the external portion thereof easily disconnected by medical personnel, leaving an indwelling portion of the assembly which is substantially flush with the entry site into the patient so as to present less of an annoyance to the patient, allow greater mobility and to maintain patient dignity.

A further object of the present invention is to provide a medical channel assembly and method which can position an easy-disconnect coupling at virtually any location along the length of the elongated channel assembly in order to enable its location flush with the patient's entry site.

Still a further object of the present invention is to provide a medical channel assembly and method which is easier for medical staff to use, is safer for the patient, is inexpensive to manufacture, can include valves and filters, and is easily held in place as inserted in the patient.

The apparatus and method of the present invention have other objects and features of advantage which will be set forth in more detail in, or be apparent from, the following description of the Best Mode Of Carrying Out The Invention and the accompanying drawings.

SUMMARY OF THE INVENTION

The elongated medical channel assembly of the present invention is comprised, briefly, of an indwelling member formed and dimensioned for positioning of an end thereof in an indwelling position in a patient, an external member, and a coupling assembly releasably coupling together the indwelling member and the external member for communication of fluid or signals therebetween at a location substantially at an exit site of the channel assembly from the patient to make gripping and/or inadvertent snagging or catching of the indwelling member less likely. Moreover, positioning of the coupling assembly at the exit site tends to provide lateral stability and thereby help secure the coupling assembly to the patient. Such securement can be augmented by securement devices such as tabs and/or tape, and very importantly, the coupling assembly is formed for angular displacement or articulation so that an applied force which is relatively low and may be oriented at a wide range of angles will disconnect the coupling before the indwelling tube is dislodged. In the preferred form the easy-disconnect coupling assembly is formed for relative articulation of the external channel-defining member relative to the internal channel-defining member, and the assembly includes an exit site securement or mounting structure. The medical channel assembly of the present invention also can include valves, filters and multiple lumen configurations.

The method of preventing inadvertent or uncooperative patient dislodgement of the indwelling portion of an elongated medical channel assembly of the present invention comprises, briefly, the steps of coupling together two lengths of channel-defining members by an easy-disconnect coupling, and inserting an indwelling length of the members into the patient until the coupling is positioned sufficiently flush to the exit site of the channel assembly from the patient that upon disconnection of the external length, the patient has great difficulty manually grasping either the indwelling length of channel-defining member or the remaining portion of the coupling assembly.

In another aspect of the present invention a method for forming a releasable connection in an elongated medical channel assembly is provided comprising, briefly, steps of mounting an indwelling coupling portion of a releasable coupling assembly to an indwelling channel-defining member at a location from an inner end of the indwelling channel-defining member positioning the indwelling coupling portion closely proximate an exit site from the patient when the elongated channel assembly is used, securing an external coupling portion of the releasable coupling assembly to an external channel-defining member, and releasably coupling the indwelling coupling portion to the external coupling portion of the coupling assembly.

BRIEF DESCRIPTION OF THE DRAWINGS

FIG. 1 is a side elevation view of a nasoenteral feeding tube assembly constructed in accordance with the present invention and shown with the external tube uncoupled from the patient and connected to an enteral nutrition pump.

FIG. 2 is a fragmentary, enlarged, side elevation view of the coupling portion of the medical tube assembly of FIG. 1.

FIG. 3 is a further enlarged, fragmentary, side elevation view, in cross section of, a slightly modified coupling portion corresponding to FIG. 2.

FIG. 4 is a side elevation view, in cross section, corresponding to FIG. 3 with the external tube coupled to the coupling assembly and in an articulated position.

FIG. 5 is a side elevation view, in cross section, of an alternative embodiment of a coupling assembly suitable for use with the medical tube assembly of the present invention.

FIG. 6 is a side elevation view, in cross section, of a further alternative embodiment of the coupling assembly of the present invention.

FIG. 7 is a bottom plan view, in cross section taken substantially along the plane of line 7—7 in FIG. 6.

FIG. 8 is a top plan view of a preferred embodiment of an indwelling tube member marked with severing indicia.

FIG. 9 is a top perspective view of a schematic representation of a drainage medical tube assembly constructed in accordance with the present invention.

FIG. 10 is further schematic representation of a syringe assembly useful with the medical tube assembly of the present invention.

FIG. 11 is a fragmentary, side elevation view of a schematic representation of an alternative embodiment of the coupling portion of the tube assembly of the present invention.

FIG. 12 is a side elevation view of an inter-cranial pressure monitoring channel assembly constructed in accordance with the present invention.

BEST MODE OF CARRYING OUT THE INVENTION

The elongated medical channel assembly and method of the present invention provide a practical, safe and effective solution to the seemingly irrepressible patient inclination to pull on medical tubes, lines and fibers, as well as the accidental snagging or catching of such elongated channel-defining assemblies and their dislodgement. When the patient pulls on the channel assembly of the present invention, a releasable coupling assembly disconnects at the exit site from the patient without disturbing the carefully positioned indwelling portion of the assembly. The nurse, doctor or medical technician then needs only to reconnect the coupling assembly since a portion of the coupling assembly remains attached to the indwelling member in the patient after disconnection or uncoupling of the external member. The remaining indwelling coupling portion is substantially flush-mounted, or even recessed, and accordingly, is relatively difficult for an obtunded or confused patient to grasp. Obtunded and confused patients can easily grasp the external member somewhere along its length, but they will typically lack the manual dexterity to pick at or remove a flush-mounted port or coupling portion.

The present medical channel assembly further most preferably includes an articulated coupling that will release easily under a wide range of angularly applied forces. Such articulation plus near-flush mounting and securement of the coupling assembly to the patient is highly effective in absorbing lateral displacement of the external channel-defining member so as to reduce traumatization of patient tissue proximate the channel assembly exit site. This is particularly important since the exit site often has been sensitized by a surgical procedure.

Moreover, in long-term feeding applications employing channel-defining tubing, the present tube assembly can have the external (supply) tube routinely disconnected from the indwelling tube (catheter) by medical personnel so that the patient is less aggravated and experiences less discomfort between feedings, as well as improved mobility and a more dignified appearance for visitation.

The apparatus and method of the present invention will be described primarily in connection with nasoenteral feeding tube applications, but it will be understood that it has application to other elongated medical channel assemblies. Drainage catheters, for example, are not infrequently deliberately pulled out by confused patients and inadvertently dislodged by hospital staff when patients are turned or transferred. In surgical procedures, the premature removal of tubes and drains often occurs at the worst possible time in the post-operative course. Often these drains were placed at the time of surgery or under computerized axial tomography guidance. Their premature withdrawal can lead to abscess formation, sepsis, the need for re-operation or even death. In addition to enteral feeding, the apparatus and method of the present invention, therefore, is suitable for use with a wide variety of medical catheters, including, intravenous catheters, anesthesiologic and critical care catheters, such as endotracheal catheters, as well as drainage catheters such as, Jackson-Pratt drains, Biliary T-tubes, Foley catheters and other catheters. Still further, patient monitoring devices often included internally positioned transducers and elongated electrical conductors or fiber optic strands which extend from the transducer to a monitoring device external to the patient. Similarly, stimulation therapy may require an implant with a connecting electrical conductor or line to a source of electrical stimulation.

Referring now to FIGS. 1 through 4, an elongated medical channel assembly constructed in accordance with the present invention and taking the form of a channel-defining tubing assembly, which is particularly well suited for nasoenteral feeding, is shown. The tube assembly, generally designated 21, includes an indwelling tube or catheter, generally designated 22, which is formed and dimensioned for positioning of an inner end 23 at a desired indwelling position in a patient 24.

This position can simply be in the patient's stomach, which presents fewer problems in placement, or it may be in the upper intestine of the patient. Such intestinal placement typically requires fluoroscopic or endoscopic placement.

Tube assembly 21 further includes an external tube 26 which can be coupled to a reservoir and/or pump assembly 20 supplying nutrients and/or medicine to the patient. Enteral nutrition pump assemblies 20 are well known in the art, for example, the enteral nutrition pump manufactured by Ross Laboratories of Columbus, Ohio, which is sold under the trademark FLEXIFLO-III. Typically, pump assembly 20 will include a flow rate adjustment input device 28, a display means 29, for visual display of the amount and/or rate of supply of fluids to the patient, an alarm enunciator 113 and an alarm light 114. Pump 20 will be connected by tube 30 to a supply reservoir, not shown.

In order to provide for connection and disconnection of external tube 26 to indwelling or catheter tube 22, tube assembly 21 of the present invention further includes a coupling assembly, generally designated 25, which is formed for releasable coupling and uncoupling of the external tube to and from the indwelling tube. Medical tube assemblies are broadly known in the prior art which include releasable coupling assemblies between an indwelling portion of tube assembly and an external portion the tube assembly. Such prior art medical tube assemblies with releasable couplings are usually formed with latched or locked coupling assemblies which must be intentionally or deliberately manipulated to be uncoupled, or they are frangible and must be replaced if uncoupled, or they require the application of an axial force to effect release. Accordingly, as thus far described, the medical tube assembly of the present invention contains elements which are broadly known in prior art medical tube assemblies. A major disadvantage of such prior art medical tube assemblies, however, has been that they are susceptible to inadvertent or uncooperative patient dislodgement or extirpation, sometimes with traumatic or even life-threatening results.

In order to reduce the instance of inadvertent or uncooperative medical channel assembly dislodgement, tube assembly 21 of the present invention is formed with the coupling assembly 25 located along the length of tube assembly 21 at a position which causes the coupling assembly to be positioned substantially at an exit site 27 of the tube assembly from the patient, in FIG. 1, the nostril of the patient's nose. In prior art medical tube assemblies, and even those assemblies having relatively easily releasable couplings, the connection has been positioned several inches away from the exit site from the patient. This positioning of the coupling assembly has at least three disadvantages. First, when the external tube is disconnected, a very substantial and grippable length of the indwelling tubing remains at a position exteriorly of the exit site. This provides the patient with a grippable length of the indwelling tube that can subsequently be pulled from its indwelling position. Thus, while prior art medical tube assemblies having easy-disconnect couplings could reduce the inadvertent dislodgement, for example, when the patient is being handled by medical technicians, they clearly would not solve the problem of the uncooperative or mentally disabled patient who is unsupervised and during such time can grasp the indwelling tube and pull the same from his or her body.

Second, the exit site of the tube assembly often inherently provides some lateral stability or support for the tube assembly. Thus, the tissues surrounding the exit site stabilize the tube assembly, making coupling release more predictable and reproducible. Positioning a coupling at a distance from the exit site, by contrast, results in the coupling assembly being free to be laterally displaced in any direction, making release of the coupling less certain.

Third, when the tubing assembly coupling is at a distance from the exit site it is more difficult to secure the coupling to the patient in a way which makes the coupling inaccessible to the patient.

Tube assembly 21 of the present invention, therefore, does not seek to anchor or secure a one piece tube assembly to the patient in a manner making its removal difficult, nor does it seek to merely place a quick-disconnect coupling somewhere along the external tube at a position remote of the exit site. Instead, the present tube assembly positions a releasable coupling 25 sufficiently close to exit site 27 so as to stabilize the coupling and so as to make it very difficult for the patient to grasp what remains of the tube assembly after disconnection of external tube 26. An indwelling coupling portion 31 of coupling 25, therefore, is secured to indwelling tube 22 and remains with tube 22 when coupling 25 is uncoupled. In the most preferred form indwelling coupling portion 31 is either substantially flush with exit site 27 or recessed inwardly with respect thereto, as shown in FIG. 1.

As used herein, the expression "exit site" shall mean the point at which a channel-defining member effectively exits the patient. In FIG. 1, exit site 27 is a natural orifice, the patient's nostril. It will be understood, however, that exit site shall also include incisions made by a physician or technician, and in other applications, such as parenteral applications, the indwelling channel-defining member may actually extend outwardly of the patient's tissues, but be covered, for example by tape or the like, as it extends along a patient's limb to exit the tape at a site which shall be deemed for the purposes of this application to be an "exit site." In such a parenteral application, the patient cannot effectively grip and remove the channel-defining member under the tape, and is only able to grip and pull the same after it exits the "exit site" at the end of the tape.

In the most advantageous form of the medical channel assembly of the present invention, coupling assembly 25 is formed for release when a very low disconnect force is applied to the external tube from virtually any direction, and tube assembly 21 is provided with an auxiliary securement or anchoring device 62, which can be used to augment the stability of releasable coupling 25 at the exit site. Thus, in the present invention a multi-directional releasable coupling is provided which is laterally secured by reason of its positioning closely proximate the exit site itself, and because the coupling is positioned at the exit site, it can have its lateral stability conveniently enhanced by a securement device, such as a deformable tab 62 or even tape.

Coupling assembly 25 of the present invention, therefore, is formed for coupling of external tube 26 from internal or indwelling tube 22 with a disconnect force that is less than the force required to dislodge indwelling tube 22 from its position in patient 24, and preferably a disconnect force which can be applied from virtually any direction. Thus, once tubes 22 and 26 are coupled together by assembly 25, the coupling assembly will release the external tube 26 without pulling indwelling tube 22 from the patient. In the preferred form, coupling assembly 25 releases under an axial force, or a laterally applied force, of about one pound, which is well below the force required to dislodge the indwelling tube from the patient in virtually all applications, particularly when enhanced with a securement device.

Release of coupling 25 under a laterally applied force can be accomplished by forming the coupling for angular displacement of external tube 26 relative to indwelling tube 22 and providing a structure which will cause release of the coupling after angular displacement and before transmission of substantial transverse forces to the patient's tissue proximate the exit site. This is most advantageously accomplished by providing a coupling assembly 25 which can articulate and will release the external tube or channel-defining member under a force applied transversely to tube 26, in any transverse direction, which also is about one pound.

In order to facilitate uncoupling of coupling assembly 25 by a physician or technician, a manually grippable member 45 optionally may be mounted to external tube 26 proximate coupling portion 43. One of the important advantages of the tube assembly of the present invention is that medical personnel can disconnect the external or supply tube after feeding. Since coupling 25 is closely proximate exit site 27, the patient is not constantly annoyed by a tube that is still coupled to him or her. In fact the patient essentially will have complete freedom of movement, which reduces patient anxiety and increases patient dignity and morale. The technician has the advantage of merely having to recouple assembly 25 in order to accomplish the next feeding. Grippable member 45 also can be brightly colored to provide an easily monitored visual indicator for technicians to see that the patient has not uncoupled the external tube. The flush-mounted coupling assembly of the present invention, therefore, has substantial advantages even for cooperative patients, and it tends to enhance the likelihood of patient cooperation.

Referring now to FIGS. 2, further details of the preferred form of multi-directional, releasable, coupling assembly 25 can be described. In order to provide for angular displacement or relative articulation of tube 26 and tube 22, coupling assembly 25 preferably takes the form of a ball and socket coupling, with the ball mounted on one of the tubes by a coupling portion secured thereto and the socket mounted to the other tube by a coupling portion. As shown in the drawing, the preferred form is for indwelling coupling portion 31 to be formed with a socket 41 that receives a ball 42 formed on an external coupling portion 43 of assembly 25. Socket 41 in FIG. 2 includes a plurality of resiliently displaceable fingers 44 that are separated by slots 46 so as to be resiliently deformable and grip ball 42 when the same is inserted into the socket.

In FIGS. 3 and 4, socket 41 does not include fingers 44 or slots 46 and is merely formed of a resiliently elastic material, such as, a natural or synthetic rubber. The amount of release or disconnect force provided by coupling 25 can be varied by selecting the amount by which fingers 44 or socket 41 extends beyond the equator of ball 42, as well as by selection of the material used to form the socket. Moreover, it is preferable that socket 41 include a chamfer 50 at the open end thereof to ease insertion of ball 42 into the socket.

As best seen in FIG. 4, the ball and socket construction of coupling 25 allows external tube 26 and external coupling portion 43 to be articulated in socket 41 while fluid flow, either gas or liquid, through the coupling can continue. Flow of fluid through lumen 47 of external tube 26 proceeds through the bore 48 of external coupling fitting 43, out discharge opening 49 and into a cavity 51 in indwelling coupling portion 31. The fluid then is communicated through opening 52 to lumen 53 of indwelling tube 22. It is preferable that indwelling coupling portion 31 be somewhat enlarged so that opening 49 is not occluded upon articulation of tube 26 to a substantial angle relative to tube 22. Thus, the enlarged cavity 51 immediately proximate socket 41 ensures the free communication of liquids and gases through easy-release coupling 25 for a wide range of relative angles between the two tubes.

It is further preferable to provide a sealing structure in socket 41 which will seal against ball 42 and yet permit articulation. Thus, in FIG. 3 two integrally formed or monolithically molded ribs 54 are provided which slidably seal against ball 41. As shown in FIG. 4, an O-ring 54a is mounted in socket 41 and sealably engages ball 42. It also would be possible to mold a rib 54 or to mount O-ring 54a to ball 42.

In the preferred form, indwelling coupling portion 31 is formed from a plastic material which can be injection molded, such as, a medical grade, resiliently deformable rubber-like polyurethane, and coupling portion 43 may be formed of a harder material which also can be injection molded, such as TEFLON or a poly olefin.

The multi-directional release feature of coupling assembly can best be understood by reference to FIG. 4. Pivoting of external tube 26 and ball 42 eventually causes a neck 56 of coupling member 43 to engage the chamfered end 50 of socket 41 so that further articulation of ball 42 acts to lever or urge ball 42 out of socket 41. This lever-action insures that the lateral displacement force on tube 26 required to uncouple the coupling is relatively low. Instead of traumatizing the patient's tissues proximate the exit site, therefore, lateral displacement of the external tube and articulation of coupling assembly 25 essentially pivots ball 42 out of socket 44.

Another advantage of a ball and socket easy-disconnect coupling is that the tubes can easily rotate about their respective longitudinal axes without uncoupling or transmitting high torsional forces to the patient.

Mounting of coupling portions 31 and 43 to the tubes 22 and 26 can be accomplished using a number of different techniques. As shown in the drawing, the inner end of coupling portion 41 includes a plurality of barbed ridges 57 having ramped sides and near perpendicular shoulders which face toward socket 41. As the end of coupling member 31 is urged into the end 58 of indwelling tube 22, therefore, the ramps permit insertion and the perpendicular shoulders of ribs 57 cooperate with the resilient end of tube 22 so as to prevent axial withdrawal and separation of the tube and coupling portion.

Similarly, external coupling portion 43 can be formed with one or more barbed ridges or shoulders 59 which receive and resist separation of end 61 of external tube 26. The external coupling is shown with a single shoulder 59, but it will be understood that multiple shoulders, as shown for coupling member 31, facing ball 42 could be provided to enhance securement of the fitting portion to tube end 61. Coupling portions 31 and 43 also can be secured using an adhesive, solvent welding, or can be molded together to eliminate the need for barbed securement ridges. It is preferred that the indwelling coupling portion 41 be frictionally secured entirely so that it can be secured in situ without any adhesives.

As is best seen in FIG. 2, that the indwelling coupling portion 31 or tube 22 carry, or have secured thereto, a securement device, generally designated 62, formed to engage the patient in a manner which will further laterally augment the stability of the flush-mounted coupling assembly, as well as increase the axial force required to remove the indwelling tube from the patient. Enhanced lateral stability cooperates with the coupling's lever-action release to ensure reproducibly low release forces, and increased axial securement further resists extirpation of the indwelling tube, as well as preventing the indwelling tube from being accidentally drawn or pulled into the patient.

In the nasoenteral form of the invention shown in the drawing, securement device 62 is provided by a deformable tab 63 which can be deformed into substantial conformance with the patient's body proximate the exit site. Thus, tab 63 is formed to be deformed to either the right or left into engagement with the patient's nose to enhance securement of the catheter tube 22 against withdrawal from the patient and against inhalation into the patient. One form of tab 63 can include a thin metallic member 64 (see FIG. 2) having openings 66 therein which is coupled to a rigid J-shaped arm 67 cushioned with a thin, plastic 68 capable of transmitting moisture vapor therethrough, such as a hydrocolloid dressing material. Such hydrocolloid dressing materials are manufactured, for example, by 3M and sold under the trademark TEGASORB. J-arm 67 is shown in the version illustrated in the drawings as being connected to indwelling coupling portion 31, and it can be integrally injection molded therewith or formed as one piece of aluminum with a longitudinal stiffening corrugation. Arm 67 also could be coupled to tube 22 proximate coupling member 31.

In addition to resisting axial dislodgement of tube or catheter 22, and preventing inhalation of the tube upon disconnection of external tube 26, securement tab 63 also supports socket 41 against angular deflection upon articulation of external tube 26. Thus, even the small amount of lateral force which is required to articulate tube 26 to a position which will cause it to be levered out of socket 41 is supported, in part, by securement tab 63, rather than entirely by the patient's nasal tissues.

As is best seen in FIGS. 1 and 2, the J-shaped arm can extend out of either of the patient's nostrils and up along one side of the nose to enable deformation of tab 63 over the bridge of the nose from either side thereof. This J-shaped configuration also allows socket 41 to be recessed slightly inside exit site 27 to make manual gripping or grasping of coupling portion 31 more difficult. The close proximity, deformation of tab 63 into conformance with the patient's nose, and the tab's thin cross section makes it difficult, although not impossible, to grasp the indwelling tube by the tab. But even then, the tab must first be peeled up and then pulled down. In order to further reduce the patient's ability to pick or pry up tab 63, a very thin halo 70 of protective adhesive dressing can be positioned as an overcoat to tab 63.

In the preferred form, tab 63 also includes a pressure-sensitive adhesive on the side of the tab which will contact the nose. A peal-off paper layer can be provided which is removed just before the tab is deformed over the nose. The adhesive should be selected so as to a minimum irritant or toxicity affect on the patient, and preferably does not act as a moisture barrier so that moisture can pass through the adhesive, the plastic 68, and even the underlying perforated metal member 64.

Drainage applications may require different auxiliary securement devices. FIG. 9, for example, illustrates an alternative auxiliary securement device 97, which is particularly advantageous for use with Jackson-Pratt drainage systems. In some applications, auxiliary securement can simply be provided by tape or an adhesive dressing.

FIGS. 5, 6 and 7 illustrate alternative embodiments of a ball and socket coupling suitable for use in the medical tube assembly of the present invention. As will be seen in FIG. 5, ball 42a engages socket member 31a which is formed with socket portions 44a which are longer on one side of socket 41a than the other. This structure causes the internal force from fluids to be oriented at an angle with respect to the downwardly facing socket opening. Thus, internal pressures in indwelling tube 22 in enteral feeding applications can be 20 psi, and temporarily rise higher, will not be as likely to blow the external tubing out of socket 41a. The lumen or bore 48a of the external coupling portion 43a can be seen to be curved in order to communicate fluid through the coupling and to cavity 51a even when the coupling is in the articulated position.

In FIGS. 6 and 7, a further alternative for communicating fluid through an easy-disconnect coupling 25b while reducing the tendency for pressure build-ups in the tube assembly to uncouple the tubes is shown. Ball 42b is received in a socket 41b which has extremely long finger portions 44b on one side thereof. The ball is formed with a central bore or lumen 48b having partitions 50 which define a plurality of circumferentially distributed openings 49b (see FIG. 7). Thus, regardless of the angular orientation about the central longitudinal axis of bore 48b, one of discharge openings 49b will communicate with cavity 51b in indwelling coupling portion 31b and yet not be axially aligned with the open end of socket 41b. Both alternative embodiments shown in FIGS. 5 and 6 can have associated sealing ridges or O-rings so as to minimize the escape of fluids during relative articulation and/or rotation of the ball and socket.

An essential aspect of the present invention is that an outer end of the indwelling channel-defining member in the channel assembly is positioned sufficiently close to the exit site to make manual grasping of the indwelling member after uncoupling of the external member very difficult. For some medical applications, including drainage and nasoenteral applications, significant variation in the length of the indwelling tube 22 may be required for optimum positioning or to accommodate patients of different stature. Accordingly, indwelling coupling portions 31 must be mounted to a tube end 58 on a tube having a length that has been either selected or cut to a size which is suitable for the particular patient. Two ways of accomplishing this end are shown in FIGS. 8 and 9.

An indwelling nasoenteral feeding tube 22c is provided in FIG. 9 with a weighted bolus tip 81 of the type well known in the art. (See, for example, U.S. Pat. No. 4,516,970.) Tube 22c has a length dimension from the end of bolus 81 to an opposite end 82 which is in excess of the length required for placement of bolus 81 in either the stomach or upper intestine. Distributed along tube 22c are a plurality of length indicia 83, which can be used to size the overall length of indwelling tube 22c to the particular patient and application. The doctor or medical technician can either use external measurements of the patient, which measurements can be related to the location of either the stomach or upper intestine, or can physically hold the tube 22c up to the exterior of the patient and then select a particular one 84 of indica 83 which will result in the tube having a length which will just exit the patient's nostril. Thus, using either technique, an indicia, such as indicia 84, can be selected for the particular patient and tube 22c severed at indicia 84. At this point, the indwelling coupling portion 31 of coupling assembly 25 can be mounted to severed end 84 of tube 22c. The tube can then be placed in the patient until end 84 with coupling portion 31 thereon is positioned at the patient's nose, as shown in FIG. 1. An external or supply tube 26 then can be coupled to socket 41 in coupling portion 31.

The result is an indwelling tube which has a length customized to the particular patient so as to insure that the coupling will be flush, or even slightly recessed, at exit site 27 from the patient. This customization can be similarly done for other types of catheters using external measurements and severing of one end of the indwelling tube or catheter.

In FIG. 9, a Jackson-Pratt brand of drainage tube 91 is illustrated. Jackson-Pratt drainage tubes are manufactured by Baxter Healthcare of Deerfield, Ill., and have a drainage ribbon or perforated tip 93 on which length indicia may be placed. Outer end 94 of tube assembly 91 can have an indwelling coupling portion 95 mounted thereto which can include a one-way or anti-reflux valve therein and have a petal-like securement structure 97 carried thereon. The petal securement device 97 can be sutured to the patient through openings 98 or taped to the patient proximate the exit site, often an incision in the body. Coupling portion 95 also includes an open-ended socket 96.

Jackson-Pratt drainage tube assemblies 91 are used with a manually squeezable suction reservoir 99 having an external tube 101 which can be provided with a ball filling 102 which mates with socket 96. The suction reservoir also is provided with an anti-reflux valve so that fluids can only be pulled into the reservoir.

The exact location of drainage ribbon inside patient can be varied by cutting indwelling tube 91 so as to position socket 96 just at an exit site from the patient. Either end of tube 91 can be severed. Thus, indicia 94 on ribbon end 93 can be severed or indicia 92 at end 94 can be used to determine the severing position. Obviously, if indicia 92 are used, fitting 95 must be inserted after the severing process, and if indica 94 are used, care must be taken not to shorten ribbon end 93 to the point that it is ineffective. It also would be possible to sever the drain ribbon end of tube 91 and mount drain ribbon 93 thereto by a barbed or ridged fitting.

The medical tube assembly of the present invention lends itself to incorporation of further enhancements or auxiliary equipment and features. As shown in FIG. 10, a syringe assembly, generally designated 110, can be provided with an external tube 26c on which an external coupling fitting 43c with ball portion 42c can be mounted. Medicine can be easily administered to the patient by disconnecting the normal supply tube 26 and connecting syringe supply tube 26c.

In FIG. 11 the respective indwelling coupling fitting 31d and external coupling fitting 43d include valves 111 and 112. The valves 111 and 112 can be provided in either or both of the coupling fittings. Moreover, such valves can take the form of check valves or one-way flow anti-reflux valves, depending upon whether or not the tube assembly is used as a drainage tube or a feeding tube. Still further, valves 111 and 112 can be actuatable upon disconnection so as to prevent fluid flow in either direction if ball 42d should come uncoupled from socket 41d for any reason. It is also possible for fluid pumping device 20 to include an alarm with an enunciator 113 and alarm light 114 which will sound an alarm upon uncoupling of coupling assembly 25. Such alarm system are well known in the art for enteral nutrition pumps and can be actuated by a pressure rise in the supply line. If, for example, the feeding tube becomes plugged, the pressure rise above a predetermined level (e.g., 28 psi) will shut down pump 20 and trigger the alarm. Alternatively, various mechanical and/or electrical devices can be used to terminate fluid flow in the event of disconnection. For example, one mechanical solution is to have a displaceable valve member which only moves to close the external tube upon application of a force just below the disconnection force so that the tube is closed just before disconnection occurs.

Similarly, filter means can be provided in external coupling portion 43 so as to filter out any particulate materials or contaminants. Preventing particulates from entering tube 22 is extremely important because occlusion of indwelling tube 22 also will require removal and repositioning of the indwelling tube. Including the filter in the supply line allows the same to be disconnected and then flushed of any particulates to clean the filter, usually by pumping the particulates through the filter. It is also possible to have a filter section which is replaceable and simply removed if it becomes plugged.

In FIG. 12, an inter-cranial pressure monitoring application for an elongated medical channel assembly constructed in accordance with the present invention is illustrated. Channel assembly, generally designated 121, is comprised of an indwelling channel-defining length 122 and an external channel-defining length 126. Coupling assembly 125 releasably couples indwelling length 122 to external length 126 for the communication of monitoring signals along channel assembly 121 across coupling 125.

As shown in the drawing, channel-defining lengths 122 and 126 are conductors, in this case a pair of electrical conductors, which communicate electrical signals, but it will be understood that the channel-defining lengths 122 and 126 could be optical fibers which communicate optical signals. Mounted internally of patient 124 is a transducer 123 which is selected to monitor a desired patient symptom or condition, such as pressure or temperature., or to act as an input transducer. An outer end 128 of external channel-defining member 126 can be coupled to a monitoring device, not shown, or to an input device, such as a stimulator, also not shown.

Releasable coupling 125 advantageously can take a form similar to coupling 25, that is, it can be a ball and socket type coupling permitting universal articulation over a wide range of angles and disconnection under an axial force or by purging of the ball out of the socket upon application of a lateral force to external channel-defining line 126. Obviously, electrical connection must be maintained through coupling 125 if the channel-defining member 122 and 126 communicate electrical signals, and optical connection must be provided for through coupling 125 if optical signals are to be communicated.

Elongated medical channel assembly 121, however, provides many of the same advantages as does tubing assembly 21. If a patient pulls on external channel-defining member 126, it will release at coupling 125 which is substantially flush with exit site 127 from the patient.

Securement augmentation petals 131 can be provided which can be taped or sutured to the patient. The patient, in any event, will have great difficulty removing or dislodging indwelling channel-defining length 122 after detachment of length 126. Once detached, the medical technician, nurse or physician can reattach the two channel-defining lengths with the assistance of manually grippable member 145 and without the need of repositioning indwelling line 122 or transducer 123.

Having described the elongated medical channel apparatus of the present invention, the present method can be described. Broadly, the present method is comprised of the steps of coupling together two members providing channel-defining lengths 22, 122 and 26, 126 to form a medical channel assembly 21, 121 by a coupling assembly 25, 125 formed for fluid flow or signal communication therethrough and formed for disconnection of the channel-defining lengths from each other by the application of a disconnection force less than a dislodgement force required to dislodge indwelling length 22, 122. Moreover, the present method further includes the step of inserting indwelling channel-defining length 22, 122 to an indwelling position in the patient's body until coupling assembly 25, 125 is positioned closely proximate an exit site 27, 127 from the patient. Thus, any attempt by the patient to remove indwelling length by gripping external tubing length is defeated by uncoupling of assembly 25, 125, which leaves the outermost end of indwelling length so close to exit site from the patient that it is very difficult for the patient to grasp and remove indwelling channel-defining length.

In the preferred method, the coupling step is accomplished by coupling together lengths 22, 122 of channel-defining members and 26, 126 by a coupling assembly 25, 125 which is formed to be releasable under an uncoupling force, usually an outward pulling force or a lateral displacement, on length 26, 126 oriented along any one of a wide range of directions. Thus, coupling together of the assembly by a ball and socket coupling provides such a structure. The present method also advantageously combines the above set forth method steps with the step of enhancing the securement of the elongated medical channel assembly 21, 121 at exit site 27, 127 against lateral axial displacement by a securement device 62, 131.

The present method can be implemented by severing an indwelling member 22, 122 which is longer than required, to the desired length while outside the patient, or by cutting the indwelling tube to length in situ. The in situ method requires the use of a tool which can grip indwelling member at a recessed position, for example inside the patient's nostril, and while gripping the indwelling member, be capable of cutting it to length and mounting an indwelling coupling portion to the indwelling member. The tool can then release its grip on the indwelling member and the external member, with its mating external coupling portion can be releasably coupled to the indwelling coupling portion.

What is claimed is:

1. An elongated medical channel assembly comprising:
   an indwelling elongated channel-defining member formed and dimensioned for positioning of an end thereof at an indwelling position in a patient;
   an external elongated channel-defining member; and
   a coupling assembly formed for relative angular displacement of said external elongated channel-defining member relative to said indwelling elongated channel-defining member without disconnection, said coupling assembly releasably coupling together said indwelling elongated channel-defining member and said external elongated channel-defining member for communication of one of a fluid and a signal therebetween at a location along a length of said medical channel assembly positioning said coupling assembly substantially at an exit site of said indwelling elongated channel defining member from said patient when said medical channel assembly is in use, and said coupling assembly being further formed for uncoupling of said external elongated channel-defining member from said indwelling elongated channel-defining member with a disconnect force less than a force required to dislodge said indwelling elongated channel-defining member as mounted in an indwelling position in said patient.

2. The elongated medical channel assembly as defined in claim 1 wherein,
   said coupling assembly is located along the length of said channel assembly at a position causing a portion of said coupling assembly connected to said indwelling elongated channel-defining member to be substantially flush with said exit site when said channel assembly is in use.

3. The elongated medical channel assembly as defined in claim 1 wherein,
   said coupling assembly is located along the length of said channel assembly at a position causing a portion of said coupling assembly connected to said indwelling elongated channel-defining member to be recessed inwardly of said exit site when said medical channel assembly is in use.

4. The elongated medical channel assembly as defined in claim 1 wherein,
   said coupling assembly is located along the length of said channel assembly at a position sufficiently close to said exit site to make manual gripping of a portion of said coupling assembly connected to said indwelling elongated channel-defining member by said patient difficult when said channel assembly is in use and said external elongated channel-defining member is disconnected from said indwelling elongated channel-defining member.

5. The elongated medical channel assembly as defined in claim 1 wherein,
   said indwelling elongated channel-defining member is provided as an indwelling tube and said external elongated channel-defining members is provided as an external tube to form a medical elongated tube assembly.

6. The elongated medical channel assembly as defined in claim 5, and
   a syringe assembly having an output tube with a coupling portion thereon formed to mate with a coupling portion carried by said indwelling tube.

7. The elongated medical channel assembly as defined in claim 5 wherein,
   said medical channel assembly is a drainage tube assembly.

8. The elongated medical channel assembly as defined in claim 7 wherein,
   said drainage tube assembly includes an indwelling tube have a perforated drainage ribbon on an inner end thereof.

9. The elongated medical channel assembly as defined in claim 5, and
   a filter mounted to one of said external tube and a portion of said coupling assembly affixed to said external tube member whereby occlusion of said indwelling tube is reduced, by said filter.

10. The elongated medical channel assembly as defined in claim 9, and
    a flushing assembly connected to one of said external tube and a coupling portion of said coupling assembly affixed to said external tube, said flushing assembly being formed to flush particulate material from said filter upon uncoupling of said external tube.

11. The elongated medical channel assembly as defined in claim 5 wherein,
    said coupling assembly is formed for multi-directional uncoupling upon application of a disconnect force to said external tube, said disconnect force oriented at an angle to said indwelling tube.

12. The elongated medical channel assembly as defined in claim 11 wherein,
    said coupling assembly is formed for uncoupling of the external tube by a substantially constant disconnect force for all angles of articulation of said external tube relative to said indwelling tube.

13. The elongated medical channel assembly as defined in claim 11 wherein,
said coupling assembly is formed for uncoupling under a disconnect force which is substantially less than a force required to dislodge said indwelling tube for all angles of a multi-directional uncoupling of said external tube.

14. The elongated medical channel assembly as defined in claim 5, and
a first valve mounted in one of said indwelling tube and said coupling assembly and formed to block fluid flow in said indwelling tube upon disconnection of said external tube, and
a second valve mounted in one of said external tube and said coupling assembly and formed to block fluid flow in said external tube upon disconnection of said external tube.

15. The elongated medical channel assembly as defined in claim 5, and
a valve mounted in one of said external tube and said coupling assembly and formed to block fluid flow through said external tube upon disconnection of said external tube.

16. The elongated medical channel assembly as defined in claim 5, and
a valve mounted in one of said indwelling tube and said coupling assembly and formed to block fluid flow through said indwelling tube upon disconnection of said external tube.

17. The elongated medical channel assembly as defined in claim 1, and
a securement device mounted to one of an indwelling coupling portion of said coupling assembly and said indwelling elongated channel-defining member formed to enhance securement of said indwelling elongated channel-defining member to said patient.

18. The elongated medical channel assembly as defined in claim 17 wherein,
said securement device is a deformable tab formed for deformation into substantial conformance with a patient's body proximate said exit site.

19. The elongated medical channel assembly as defined in claim 17 wherein,
said securement device is a petal-like securement structure formed for at least one of suturing and taping to said patient proximate said exit site.

20. The elongated medical channel assembly as defined in claim 1, and
an alarm device coupled to said channel assembly, said alarm device actuated upon at least one of occlusion of said channel assembly and uncoupling of said coupling assembly.

21. The elongated medical channel assembly as defined in claim 1 wherein,
said coupling assembly includes an indwelling coupling portion secured to said indwelling elongated channel-defining member and an external coupling portion secured to said external elongated channel-defining member, said indwelling coupling portion and said external coupling portion being formed with a pair of mating cooperative releasable coupling structures.

22. The elongated medical channel assembly as defined in claim 21 wherein,
said mating cooperative releasable coupling structures are provided by a ball and a socket.

23. The elongated medical channel assembly as defined in claim 22 wherein,
said socket is provided on said indwelling coupling portion and said ball is provided on said external coupling portion.

24. The elongated medical channel assembly as defined in claim 22 wherein,
said indwelling elongated channel-defining member and said external elongated channel-defining member are both tubes; and
said ball and said socket each have a passageway therethrough formed and oriented for communication of fluid through said coupling assembly for a wide range of angles of articulation of said ball relative to said socket.

25. The elongated medical channel assembly as defined in claim 24 wherein,
said indwelling coupling portion of said coupling assembly includes at least one barbed securement ridge formed to be urged into telescoped relation with an end of an indwelling tube to mechanically secure said coupling indwelling portion to said indwelling tube.

26. The elongated medical channel assembly as defined in claim 24 wherein,
at least one of said ball and said socket include a seal positioned to seal fluid communication through said coupling assembly for all articulated positions.

27. The elongated medical channel assembly as defined in claim 1 wherein,
said indwelling elongated channel-defining member includes a plurality of length indicia thereon for severing of said indwelling elongated channel-defining member to a desired length to position said coupling assembly close to the said exit site.

28. The elongated medical channel assembly as defined in claim 26 wherein,
said indwelling elongated channel-defining member is provided as an indwelling tube and said external elongated channel-defining member is provided as an external tube; and
said indwelling tube includes a perforated tip at an inner end thereof; with length indicia provided on said perforated tip.

29. The medical channel assembly as defined in claim 1 wherein,
said indwelling channel-defining member, said external channel-defining member and said coupling assembly are each formed for communication of one of patient monitoring and patient stimulating signals therethrough.

30. The medical channel assembly as defined in claim 29 wherein,
said indwelling channel-defining member and said external channel-defining member are elongated electrical conductors.

31. The medical channel assembly as defined in claim 30, and
a transducer device electrically connected proximate an innermost end of the indwelling electrical conductor.

32. A nasoenteral tube assembly comprising:
an indwelling catheter;
an external supply tube; and
a releasable coupling assembly coupling together said external supply tube to said indwelling catheter for fluid flow therebetween and said releasable coupling assembly formed for relative angular displacement of said external supply tube relative to said indwelling catheter without disconnection, said indwelling catheter having a length dimension positioning said releasable coupling assembly sufficiently close to a nose of a patient, when in use, to enhance lateral stability of said releasable coupling assembly and to make manual grasping of said indwelling catheter and a portion of said releasable coupling assembly carried by said indwelling catheter very difficult, and said releasable coupling assembly being formed for uncoupling prior to dislodgement of said indwelling catheter from an indwelling position in said patient.

33. The nasoenteral tube assembly as defined in claim 32 wherein, said indwelling catheter has a length, and said releasable coupling assembly is formed, to position said portion of said releasable coupling assembly carried by said indwelling catheter at one of: (i) a position substantially flush with said nose, and (ii) a position recessed inwardly of said nose.

34. The nasoenteral tube assembly as defined in claim 32 wherein, said releasable coupling assembly is formed for articulation of said external supply tube relative to said indwelling catheter while maintaining fluid flow.

35. The nasoenteral tube assembly as defined in claim 34 wherein, said releasable coupling assembly is formed for disconnection under a force applied axially to said external supply tube which is substantially equal for substantially all angles of articulation and is formed for disconnection under a transversely applied force which is substantially equal to said force applied axially.

36. The nasoenteral tube assembly as defined in claim 32 wherein, said releasable coupling assembly is formed for multi-directional disconnection.

37. The nasoenteral tube assembly as defined in claim 32, and a securement device carried by one of said releasable coupling assembly and said indwelling catheter and formed to engage said nose to enhance securement of the indwelling catheter to said nose against withdrawal from an indwelling position in the patient.

38. The nasoenteral tube assembly as defined in claim 37 wherein, said releasable coupling assembly is formed for articulation of said external supply tube relative to said indwelling catheter, and said securement device is formed to support said indwelling catheter against angular deflection upon articulation of said supply tube.

39. The nasoenteral tube assembly as defined in claim 37 wherein, said securement device is a deformable tab formed for deformation into substantial conformance with said nose.

40. The nasoenteral tube assembly as defined in claim 39 wherein, said tab is mounted to a J-shaped arm formed to extend out of either one of the nostrils of said nose and up along side the nose, and said deformable tab formed for deformation of said deformable tab over the bridge of the nose from either side of the nose.

41. The nasoenteral tube assembly as defined in claim 40 wherein, said tab carries a pressure-sensitive adhesive thereon and is formed for moisture transmission through said tab.

* * * * *

UNITED STATES PATENT AND TRADEMARK OFFICE
CERTIFICATE OF CORRECTION

PATENT NO. : 5,645,539

DATED : July 8, 1997

INVENTOR(S) : SOLOMON et al.

It is certified that error appears in the above-indentified patent and that said Letters Patent is hereby corrected as shown below:

At Column 10, line 60 delete "Fig. 2 that" and insert therefor --Fig. 2. It is further desirable that--.

At column 18, claim 28, line 37 delete "26" and insert therefor --27--.

Signed and Sealed this

Eighteenth Day of November 1997

Attest:

BRUCE LEHMAN

Attesting Officer

Commissioner of Patents and Trademarks